(12) United States Patent
Wilson et al.

(10) Patent No.: US 10,813,747 B2
(45) Date of Patent: Oct. 27, 2020

(54) EXPANDABLE DEVICE FOR CAPTURING REGURGITANT JET, VOLUME, AND FORCE TO EFFECT VENTRICULAR FUNCTION AND REMODELING

(71) Applicant: Harmony Development Group, Inc., Cornelius, NC (US)

(72) Inventors: John Wilson, Cornelius, NC (US); Christopher Seguin, Norton, MA (US); Nikola Cesarovic, Volketswil (CH)

(73) Assignee: Harmony Development Group, Inc., Cornelius, NC (US)

( * ) Notice: Subject to any disclaimer, the term of this patent is extended or adjusted under 35 U.S.C. 154(b) by 0 days.

(21) Appl. No.: 15/863,438

(22) Filed: Jan. 5, 2018

(65) Prior Publication Data

US 2018/0185141 A1 Jul. 5, 2018

Related U.S. Application Data

(60) Provisional application No. 62/442,861, filed on Jan. 5, 2017.

(51) Int. Cl.
*A61F 2/24* (2006.01)
*A61F 2/00* (2006.01)

(52) U.S. Cl.
CPC ......... *A61F 2/2403* (2013.01); *A61F 2/0077* (2013.01); *A61F 2/246* (2013.01); *A61F 2/2481* (2013.01); *A61F 2/2487* (2013.01); *A61F 2/2412* (2013.01); *A61F 2/2421* (2013.01); *A61F 2/2457* (2013.01); *A61F 2002/0081* (2013.01); *A61F 2220/0008* (2013.01);

(Continued)

(58) Field of Classification Search
CPC ....................................................... A61F 2/24
See application file for complete search history.

(56) References Cited

U.S. PATENT DOCUMENTS 7,854,762 B2 12/2010 Speziali et al.
9,050,189 B2 6/2015 Padala et al.
(Continued)

OTHER PUBLICATIONS

International Search Report and Written Opinion for PCT/US2018/012586, dated Mar. 20, 2018.

*Primary Examiner* — Matthew W Schall
(74) *Attorney, Agent, or Firm* — Stephen J. Kenny; Robert Piston; Foley Hoag LLP (57) ABSTRACT

An implant system for capturing a regurgitant jet to effect preserving the atrioventricular pressure gradient and ventricular remodeling in a human heart including an expandable implant for positioning in the atrial/ventricular valve of the human heart and at least partially within the atrium and/or the ventricle, the expandable implant defining a first position for at least partially capturing the atrioventricular pressure gradient and regurgitant trans-valvular blood flow and associated driving forces during systole and a second position for steering flow from the atrium to the ventricle to enhance vorticular flow during diastole; a therapeutic apical base plate attachable to the apex of the heart; and a tethering conduit connected between the expandable implant and the therapeutic apical base plate assembly that transducts the energy and/or forces of captured regurgitant trans-valvular blood flow or atrioventricular pressure to the structures of the ventricle and the ventricular wall.

14 Claims, 9 Drawing Sheets

(52) U.S. Cl.
CPC ............... *A61F 2220/0025* (2013.01); *A61F 2230/0093* (2013.01); *A61F 2250/0007* (2013.01); *A61F 2250/0008* (2013.01)

(56) References Cited

U.S. PATENT DOCUMENTS

| | | |
|---|---|---|
| 9,498,330 B2 | 11/2016 | Solem |
| 2006/0058871 A1 | 3/2006 | Zakay et al. |
| 2006/0241745 A1 | 10/2006 | Solem |
| 2007/0270943 A1 | 11/2007 | Solem et al. |
| 2013/0325110 A1 | 12/2013 | Khalil et al. |
| 2014/0309732 A1* | 10/2014 | Solem ................... A61F 2/246 623/2.36 |
| 2016/0113765 A1 | 4/2016 | Ganesan et al. |
| 2016/0317290 A1 | 11/2016 | Chau et al. |

* cited by examiner

EXPANDABLE DEVICE FOR CAPTURING REGURGITANT JET, VOLUME, AND FORCE TO EFFECT VENTRICULAR FUNCTION AND REMODELING

CROSS-REFERENCE TO RELATED APPLICATIONS

This application claims priority to U.S. Provisional Patent Application No. 62/442,861 filed on Jan. 5, 2017, entitled "Expandable Device for Capturing Regurgitant Jet, Volume, and Force To Effect Ventricular Function and Remodeling," which is hereby incorporated by reference in its entirety herein.

TECHNICAL FIELD

The present disclosure relates generally to an expandable implant to capture, contain, and re-direct the native energy and force of the atrioventricular pressure gradient and the subvalvular structures using atrioventricular forces and the regurgitant jet itself, taking native or pathological sources of energy and force and re-directing them to assist ventricular function and facilitate reverse remodeling, within the heart of a human subject. Further, present disclosure relates generally to an expandable implant for capturing and harnessing the forces of aberrant atrioventricular pressure gradient and blood flow, transducting, and imparting those forces upon the ventricle and the ventricular wall of the heart.

SUMMARY

An implant system for improving or restoring normal healthy physiological cardiac hemodynamic flow and valvulo-ventricular force interaction in a human heart is provided including an expandable implant for positioning at least partially within the atrium, the ventricle, and the atrio-ventricular valve of the human heart and defining a first position for capturing regurgitant (e.g., aberrant) transvalvular blood flow, preserving the atrioventricular pressure gradient within the ventricle, and securing its driving forces from loss during systole and a second position for steering flow from the atrium to the ventricle facilitating, assisting, or enhancing physiologic vorticular flow during formation in diastole, a therapeutic apical base plate assembly attachable to the apex of the heart, and a tethering conduit or shaft connected between the expandable implant and the therapeutic apical base plate assembly that transducts the energy and force of captured atrioventricular pressure gradient, the valvulo ventricular forces, and regurgitant jet flow to the heart structures of the ventricle and the ventricular walls.

In some embodiments, the expandable implant defines an expandable skirt-shaped barrier located in the atrium or the ventricle or both.

In some embodiments, the expandable implant has angled ridges (vortical flow facilitating ridges)

In some embodiments, the expandable implant is connected to the tethering conduit or shaft by a multitude of elements (struts, cords, or filaments) that may determine the size and the shape of the maximal opening and volume of the expandable implant.

In some embodiments, the size and the shape of the maximal opening and volume of the expandable implant is adjustable by changing the length of the struts, chords or filaments.

In some embodiments, the first position is in an open position of the expandable implant, and the second position is a closed position of the expandable implant.

In some embodiments, the therapeutic apical base plate assembly comprises a securement plate and ball-joint.

BRIEF DESCRIPTION OF THE DRAWINGS

The objects, features and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein.

DETAILED DESCRIPTION

Figure 1:
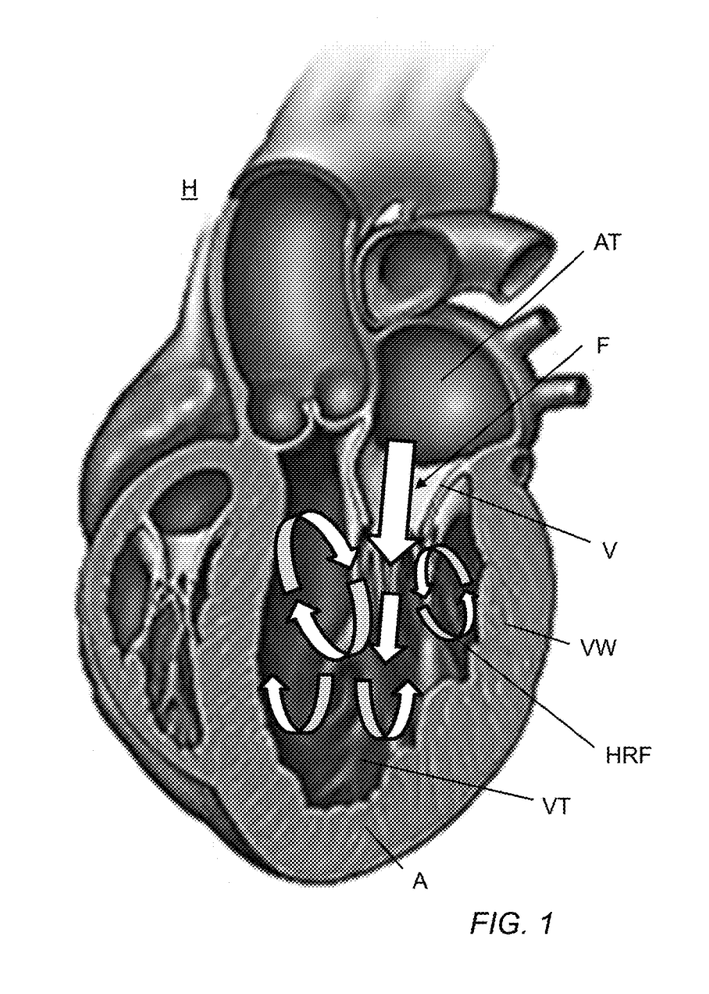
FIG. 1 is a diagram illustrating the vortex flow pattern of a healthy human heart.

One of the features of healthy heart function is proper physiological intracardiac flow. During contraction, ventricular systole, of the ventricle VT, considerable forces, generated by atrioventricular pressure gradient, are exerted on the closed atrial/ventricular valve V. These forces are transducted via the chordae tendinae and papillary muscles to the ventricle and the ventricular wall VW. There is a resulting valvulo-ventricular wall interaction, which provides the ventricle VT with structural support and stability by maintaining the elliptical geometry and functional support, which is pivotal for healthy intracardiac hemodynamic flow, supports the creation of healthy ventricular vortices, and delivers energy, force, and velocity during ventricular ejection. During ventricular diastole, the ventricular pressure rapidly decreases allowing the ventricle to fill. The pressure gradient between the atrium and the ventricle is referred to as the atrioventricular pressure gradient. The valve opens and blood rushes from the higher pressure atrium AT into the lower pressure ventricle VT through the orifice of the valve V in the direction of flow (indicated by arrow F). The valve leaflets have a steering function, directing ventricular flow at an angle to create initial spin as illustrated in FIG. 1. Such angle may be due to the asymmetry of the valve leaflets and/or to the different shapes and sizes of the leaflets. A vortex progression culminates in the creation of a healthy ventricular vortex It is believed that the ventricular/apical countertwist initiates diastole, and the inflowing ventricular blood flows off the leaflets at vector. This exit of blood through the valve orifice and off of the valve leaflet begins the initial spin. The filling of the ventricle and pressure creates a 'hemoskeleton', which acts or functions like a fulcrum, and the ventricular/apical countertwist then engages the this hemodynamic spin, such that a vortex is created in the ventricle VT. The resulting rotational flow or vortex HRF, now a reservoir of kinetic energy within the ventricle, is believed significant to proper blood flow velocity and volume through and out of the heart.

Figure 2:
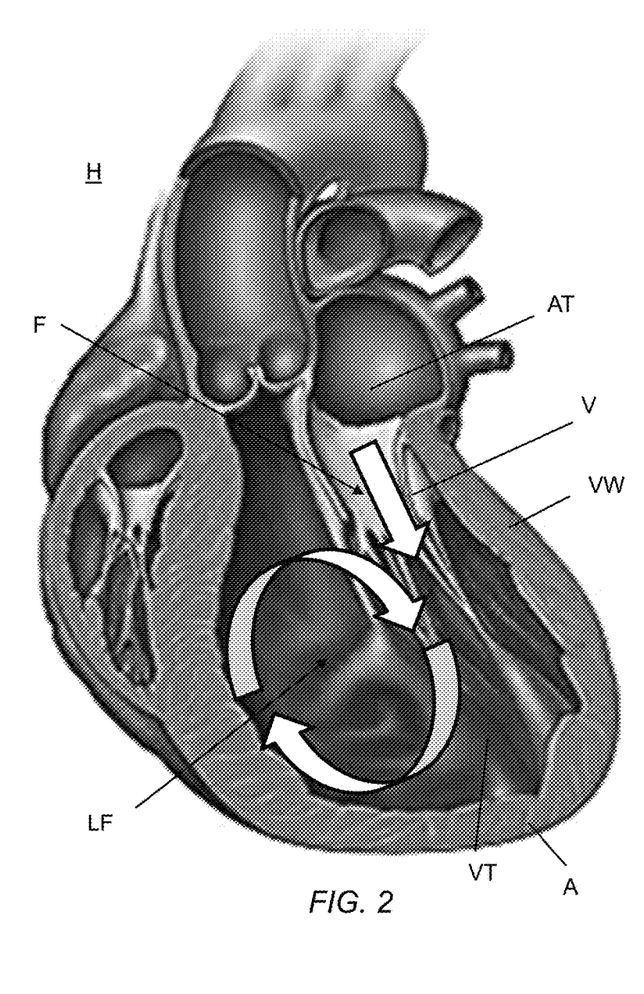
FIG. 2 is a diagram illustrating the dysfunctional vortex flow pattern of a human heart with DCM.

FIG. 2 illustrates that under certain conditions, such as dilated cardiomyopathy (DCM) in which the heart H becomes enlarged, the vortex and elliptical shape are lost, and the ventricle VT is unable to pump blood efficiently. Such conditions are marked by a low velocity flow LF and poor cardiac output in which the vortices are abnormal or absent and geometric distortion is present.

In accordance with the disclosed subject matter, a regurgitant skirt barrier is implanted in the heart. It is anchored at the apex and extends through the valve orifice into the atrium. The atrioventricular pressure gradient, in systole, causes atrial pressure to increase and ventricular pressure to drop thus allowing the ventricle to fill. The artioventricular pressure gradient, in systole is reversed thus causing or forcing the valve leaflets to close. When the ventricle contracts in systole, the regurgitant skirt barrier is disposed in an open position and catches the regurgitant blood or 'jet' and its energy and force, preventing the loss of atrioventricular pressure, that can be lost in backflow toward and into the atrium and then transfers or transducts that energy and force, pathologic and native, to the apex, via the tethering conduit shaft, in the form of stretching and torsion, to the ventricle and ventricular wall. This force transduction, prevention of atrioventricular pressure gradient loss, and the energy and force capture, harness, and re-direction (transduction) to the ventricle and ventricular walls is critical to restore, enhance, and maintain ventricular function, health, and output. When the ventricle relaxes in diastole, the structure of the regurgitant skirt barrier is closed and may impart vector into and vorticity (i.e., spin) to the blood draining into the ventricle. By implanting the regurgitant skirt barrier, the atrioventricular pressure gradient loss and blood vortex flow pattern that is disrupted in cardiac disease can be restored and the regurgitation contained.

In one embodiment, the implant is an expandable barrier or skirt. The skirt is capable of expanding and contracting during the contraction and expansion of the heart structure.

Figure 3:
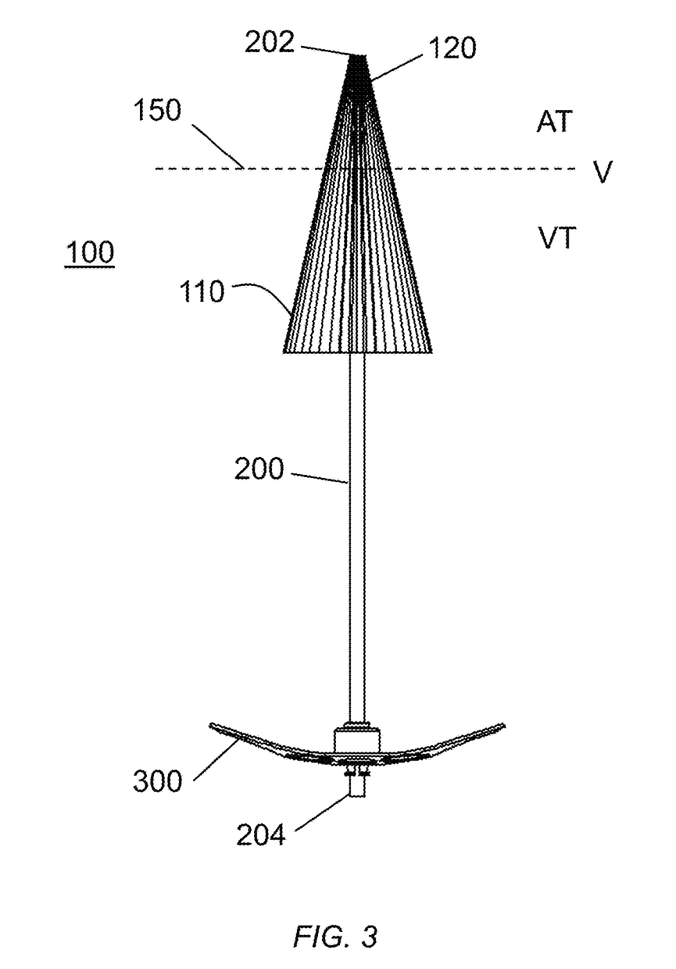
FIG. 3 illustrates the system in accordance with an exemplary embodiment of the disclosed subject matter.

As illustrated in FIG. 3, the implant device 100 includes an expandable barrier, e.g., an umbrella-shaped pleated skirt 110 with an inflow-oriented ridge 120. In some embodiments, the skirt 110 has a smooth configuration. Skirt 110 is designed for positioning in the valve orifice V, that captures the atrioventricular pressure loss or the regurgitant 'jet' or valvular backflow volume and its driving force (e.g., the volume of the regurgitant jet multiplied by the mass of the jet multiplied by jet velocity change (e.g., deceleration) generated by the atrioventricular pressure gradient). FIG. 3 illustrates the approximate location of coaptation by the valvular structure denoted by dotted line 150. The approximate atrial location AT and ventricular location VT are illustrated in the figure relative to the location of coaptation 150.

The skirt 110 is connected at the ridge portion 120 to a distal end portion 202 of a transducting shaft 200 (or force transducting tether) at the ridge portion 120. In some embodiments, the shaft is hollow having the distal 202 and proximal 204 ends closed and sealed. The transducting shaft 200 is designed to be fixed to the apex A of the heart H by an apical base plate assembly 300. (Implantation of the device 100 in the heart H is illustrated herein below in FIGS. 11-13.) The shaft 200 functions as a force transducting conduit.

The expandable skirt 110 provides improved flow during ventricular filling and no impairment during ventricular contraction. In systole, the skirt 110 is open (e.g., like an open bag), see FIG. 4, using the ventricular backflow pressure as its inflation power, becomes an atrioventricular pressure gradient loss or regurgitant 'jet' barrier that captures the backflow pressure and blood volume, contains said volume, while simultaneously capturing the negative, lost, or wasted force in said atrioventricular pressure gradient or regurgitant 'jet'. The mouth portion 160 is adjustable, and enlarged in the open configuration. In diastole the skirt 110 closed (e.g., like a collapsed bag), see FIG. 5, using the inflow pressure (from the atrium AT to the ventricle VT) as its power, returns this captured blood to the ventricle VT as it closes (by forcing the blood out of the skirt 110). The mouth portion 160 is smaller in the closed configuration. This cycle continuously repeats as the heart beats.

Figure 4:
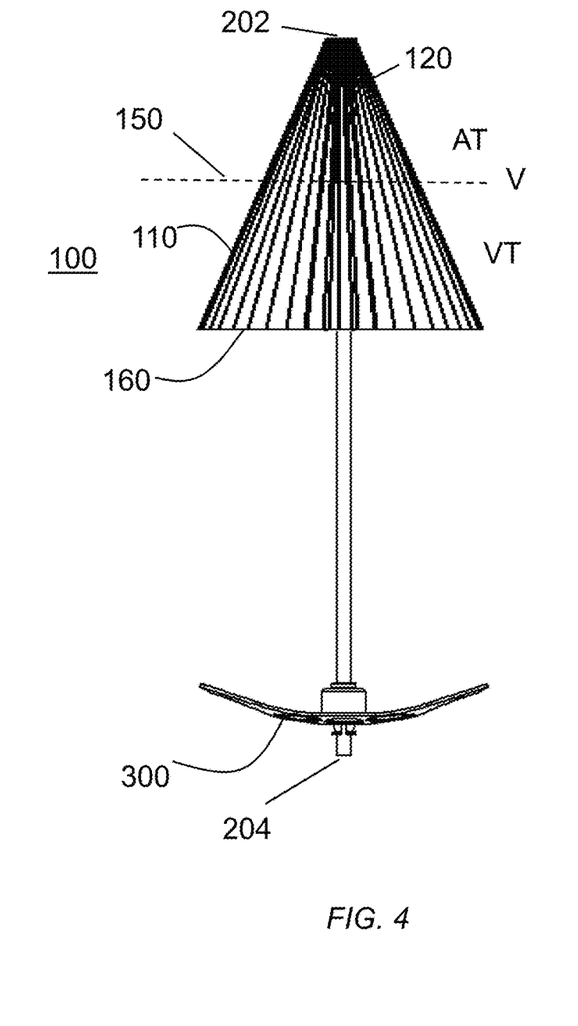
FIG. 4 illustrates the system in an open position in accordance with an exemplary embodiment of the disclosed subject matter.
Figure 5:
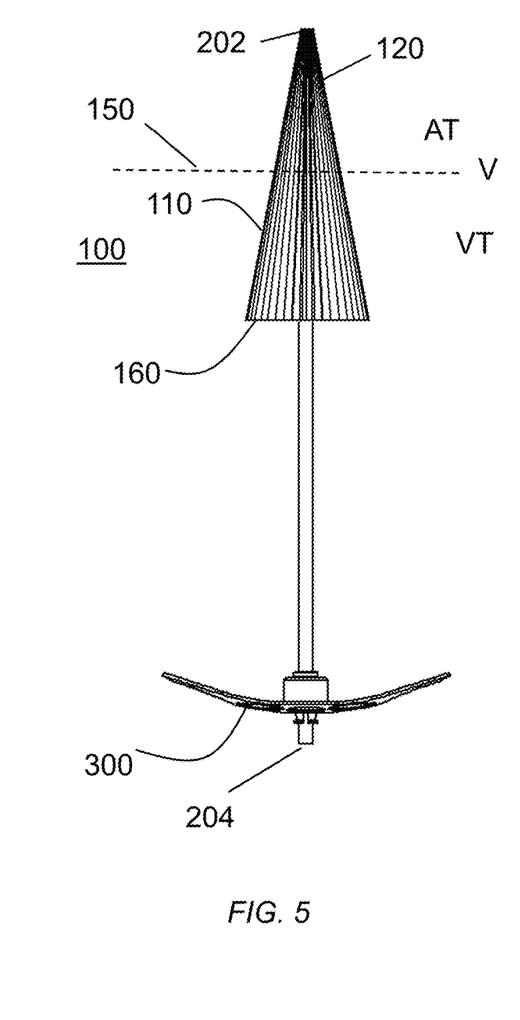
FIG. 5 illustrates the system in a closed position in accordance with an exemplary embodiment of the disclosed subject matter.

The native force of the atrioventricular pressure gradient, via the valvular and subvalvular structures, is captured as the valve leaflets coapt or "grab and pull' on the skirt 110 (e.g., at the coaptation location 150). The shaft 200, affixed the skirt 110 at one end, delivers the captured energy and force of the atrioventricular pressure gradient to the apical base plate assembly 300 being fixed onto the apex A of the heart H.

Figure 6:
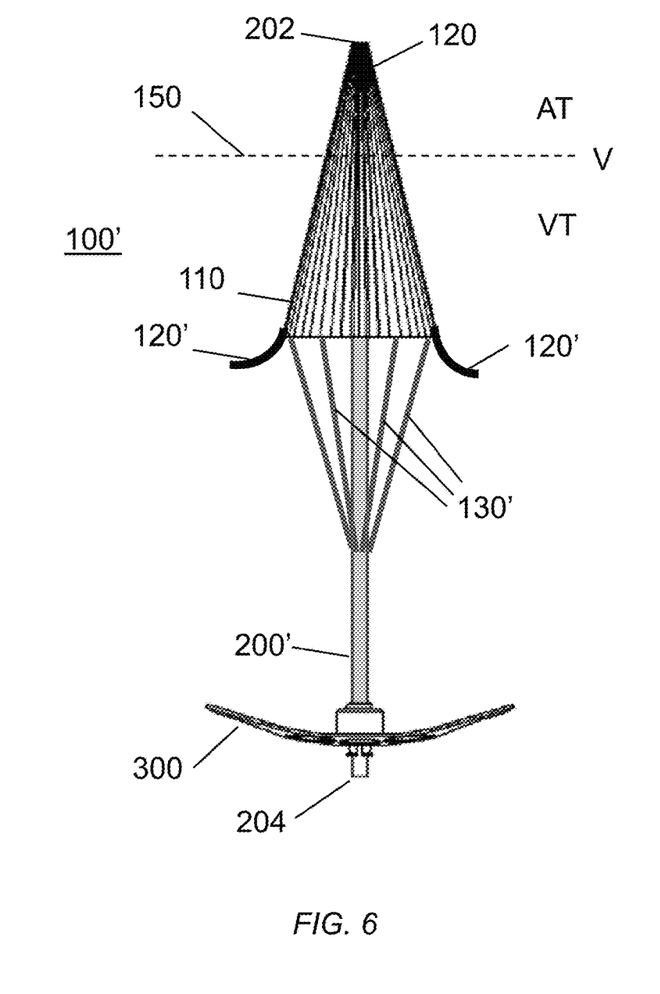
FIG. 6 illustrates the system in accordance with another exemplary embodiment of the disclosed subject matter.
Figure 7:
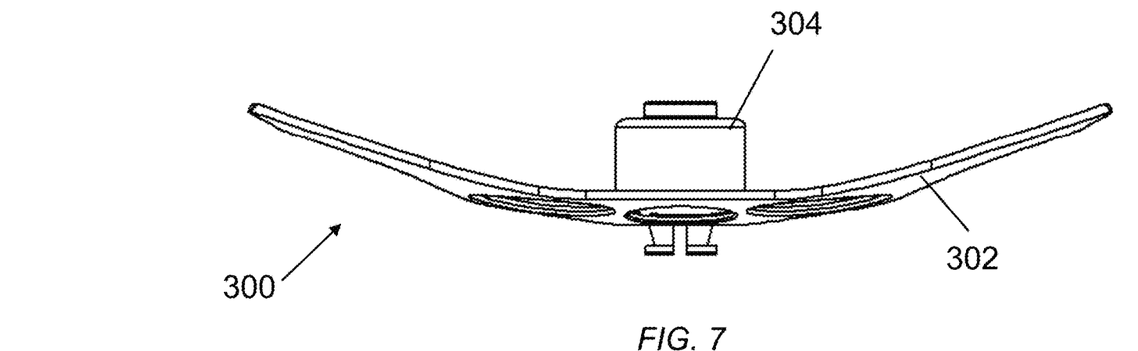
FIG. 7 is a side view of the therapeutic apical base plate assembly in accordance with exemplary embodiments of the disclosed subject matter.
Figure 8:
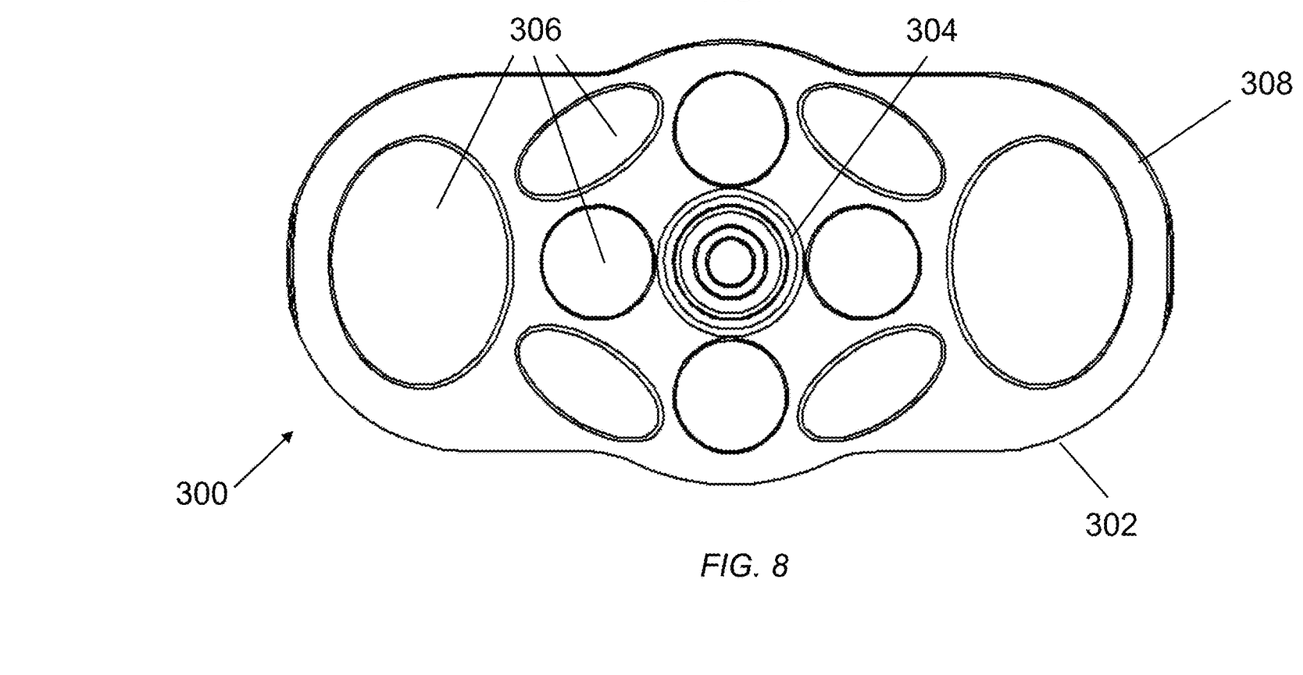
FIG. 8 is top view of the therapeutic apical base plate assembly in accordance with exemplary embodiments of the disclosed subject matter.
Figure 9:
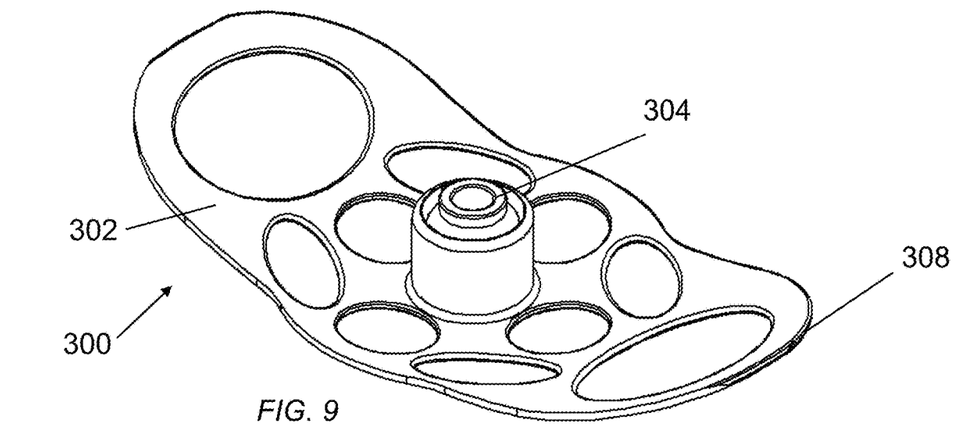
FIG. 9 is perspective view of the apical base plate assembly in accordance with exemplary embodiments of the disclosed subject matter.
Figure 10:
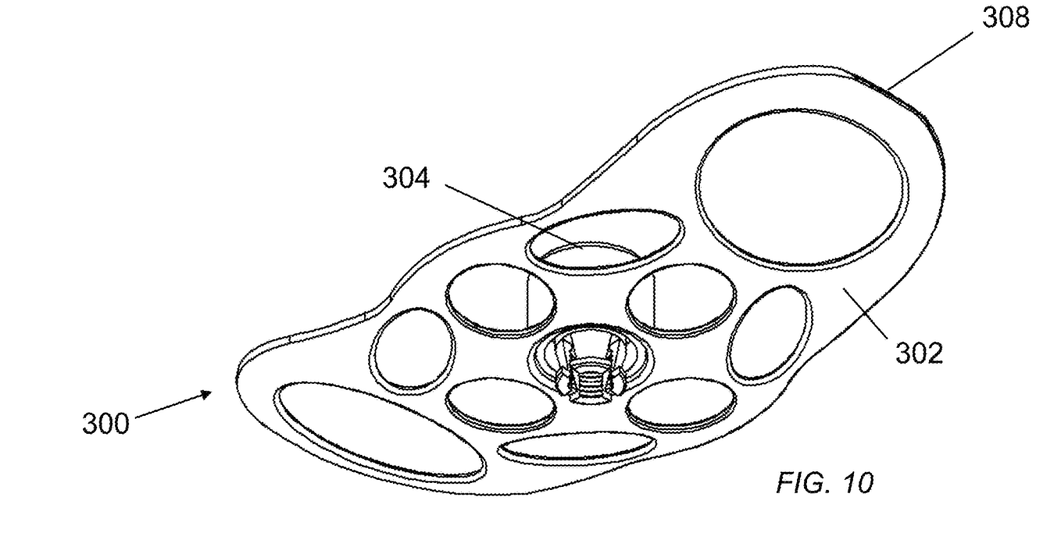
FIG. 10 is perspective view of the apical base plate assembly in accordance with exemplary embodiments of the disclosed subject matter.

FIG. 6 illustrates another embodiment of the implant device, denoted 100' herein. Implant 100' is substantially identical to the implant device 100 described above, with the following differences noted herein. Implant 100' includes diastolic blood-flow vectoring ridges 120'. Ridges 120' facilitate vortex formation in diastole. In systole as the skirt 110 fills and changes shape to a 'bag.' Ridges 120' 'invert' to provide an angled surface for the creation of vectored flow while skirt 110 provides for capturing the pressure gradient via transducting coaptation and 'grab and pull' forces. Implant 100' further includes regurgitant jet force transducting struts/filaments/strings. They also adjust the opening diameter of the skirt in systole, hence adjusting the force. Longitudinally adjustable shaft 200' is connected to the struts 130'. Together with the struts 130', the shaft 200' is useful for adjusting the opening diameter of the skirt 110.

FIGS. 7-10 illustrate therapeutic apical base plate assembly 300 including the base plate 302 and a ball jointed portion 304. In some embodiments, round oval cutouts 306 are defined in the base plate 302 to allow fibrous tissue in-growth for long-term security.

Figure 11:
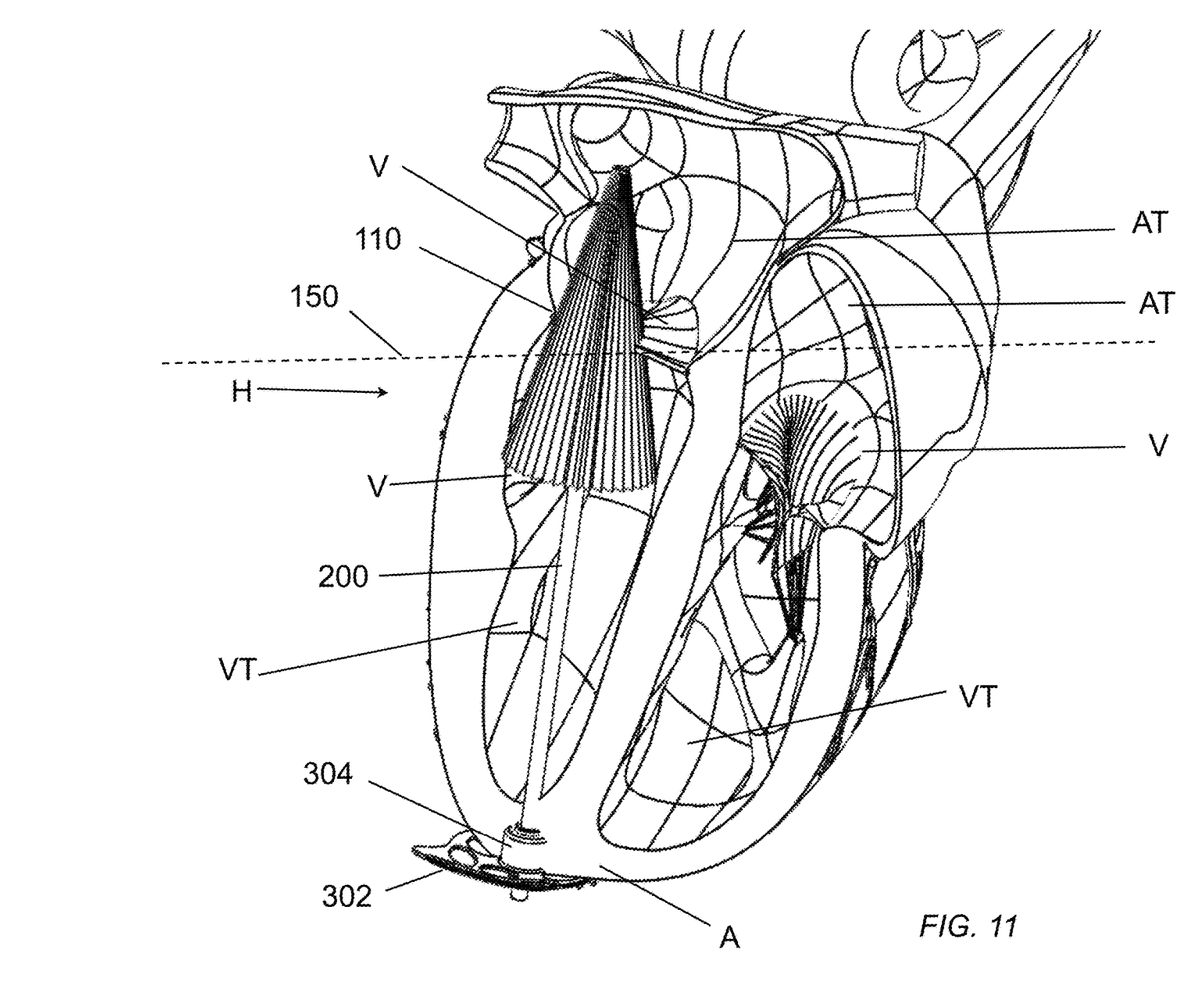
FIGS. 11-13 are views in partial section of the system of FIG. 3 installed in the human heart in accordance with exemplary embodiments of the disclosed subject matter.
Figure 12:
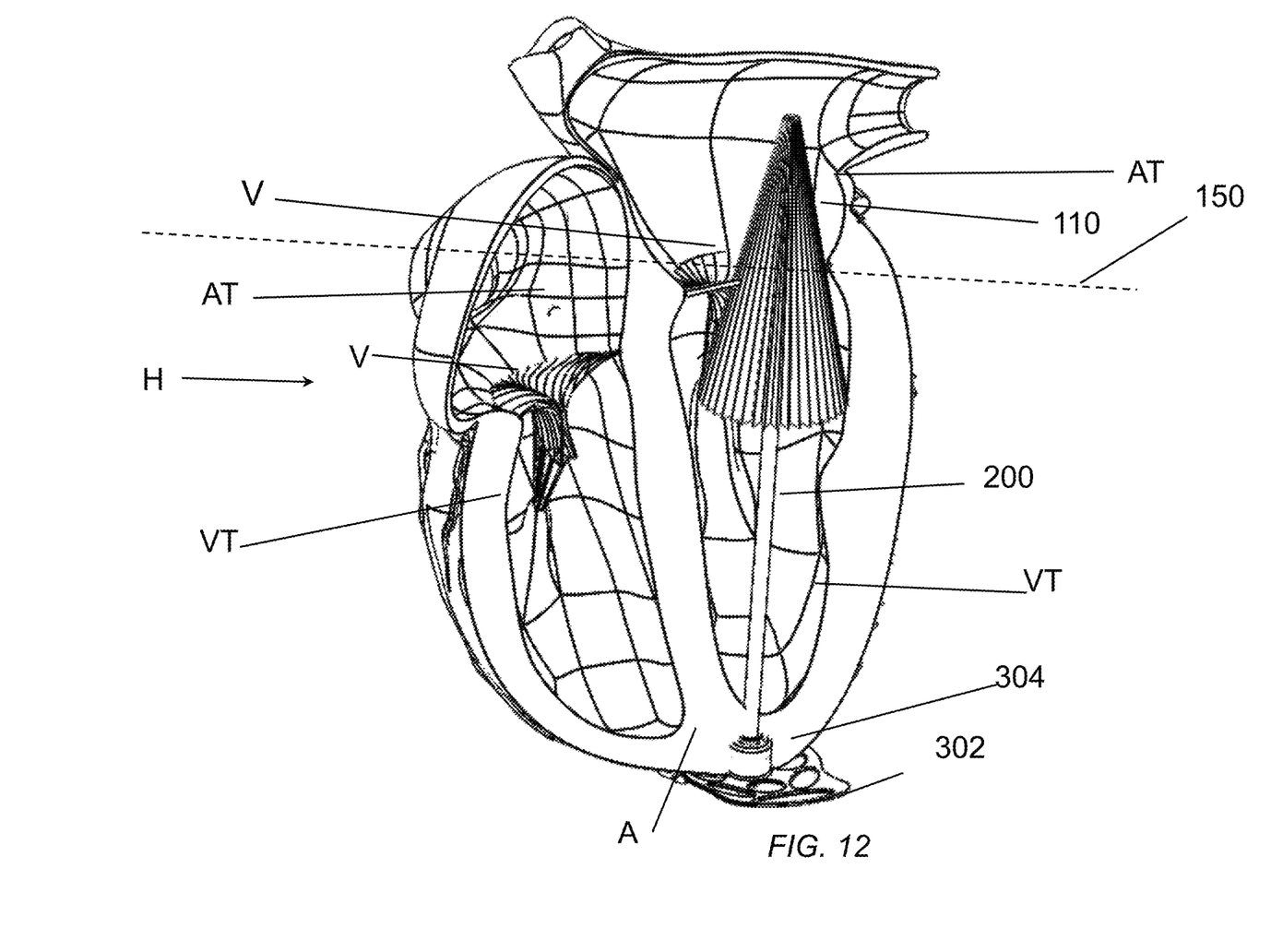
Figure 13:
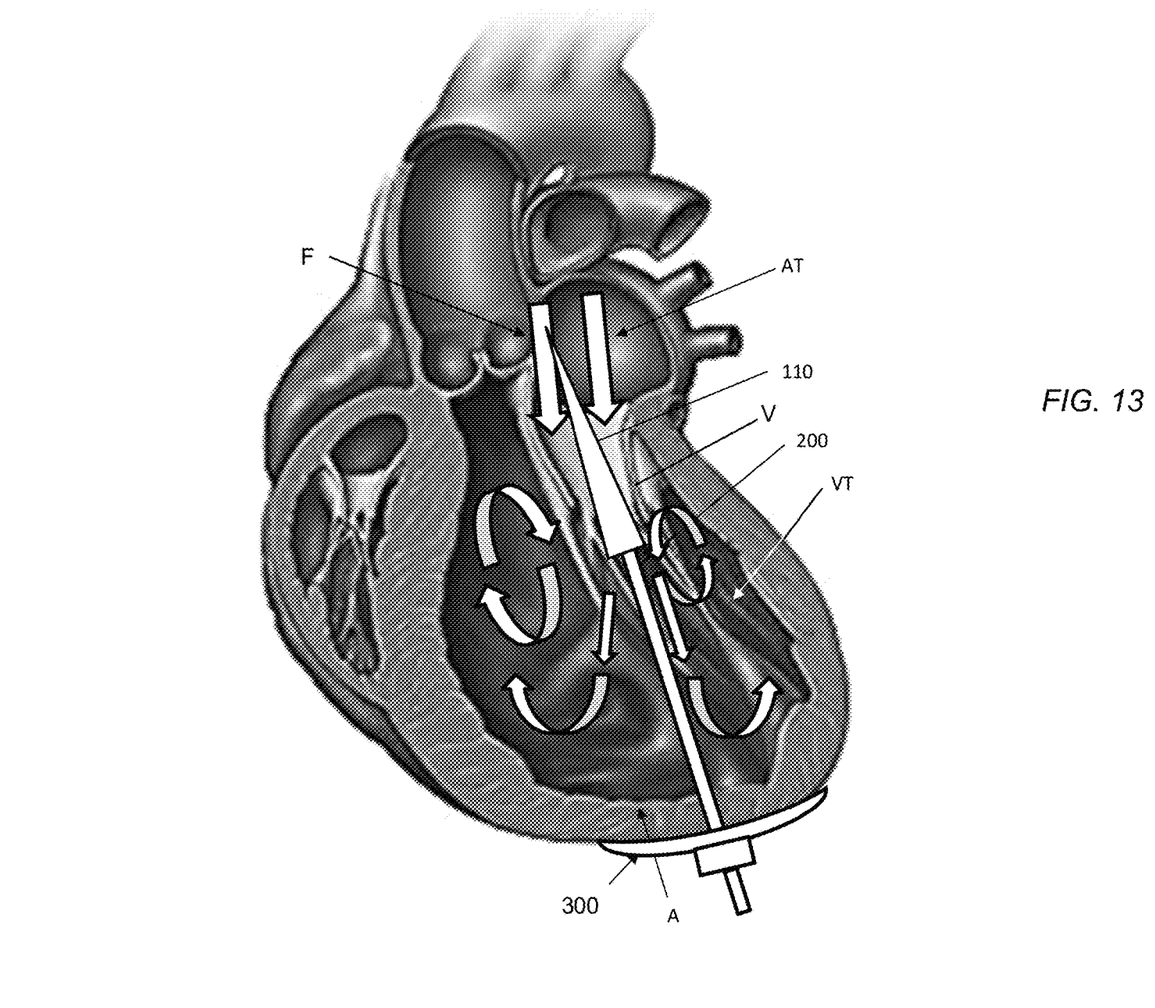

FIGS. 11-13 illustrate placement of the implant 100 in the heart H of a subject. The 'grabbing and pulling' of the skirt 110 by the valvular and subvalvular structures V (more precisely described as atrio-ventricular pressure gradient forces acting on exposed, e.g., opened, area of the skirt thus opening and closing it as well as forcing the valve leaflets to open and close) replaces lost native valvular and subvalvular force interaction (driven by the systolic atrioventricular pressure gradient) with the ventricle and ventricular walls by transducting this native force via the therapeutic apical base plate 302, to and contact with the apex A and ventricle VT. The configuration delivers physiologic natural force into the ventricular structure and into the ventricular walls thereby inducing reverse remodeling (positive geometric reshaping) of that ventricular structure VT. The base plate 302 utilizes specific edge shapes 308 to tailor the transducting of force from the apex A. By virtue of the positioning of the member 110 in the valvular and subvalular structures V, the base plate 302 pulls the apex A upward in systole and releases the apex A in diastole. In conjunction with the elongated therapeutic extensions 310 of the apical base plate 302 extending up the sides of the ventricle VT, this transducted energy is imparted by contact, specific shape, and fixation into the ventricle VT, inducing a physiologic response by replacing the lost valvulo-ventricular interaction required to maintain healthy geometric ventricular shape.

It will be appreciated that the methods and systems described above are set forth by way of example and not of limitation. Numerous variations, additions, omissions, and other modifications will be apparent to one of ordinary skill in the art. Thus, while particular embodiments have been shown and described, it will be apparent to those skilled in the art that various changes and modifications in form and details may be made therein without departing from the spirit and scope of this disclosure and are intended to form a part of the disclosure as defined by the following claims, which are to be interpreted in the broadest sense allowable by law.

What is claimed is:

1. An implant for capturing a regurgitant jet in a human heart, the implant comprising:
   an expandable barrier comprising a conical skirt having a plurality of pleats, the expandable barrier extending proximally from a first end having a first diameter to a second end having a second diameter, wherein the second diameter is greater than the first diameter;
   a shaft having a proximal end and a distal end, the distal end of the shaft operably coupled to the first end of the expandable barrier, wherein a plane defined by a circumference at the second end of the expandable barrier intersects an intermediate position along the shaft between the proximal end and the distal end; and
   an apical base plate assembly operably coupled to the proximal end of the shaft;
      wherein the expandable barrier is configured to at least partially capture forces from an atrioventricular pressure gradient and transvalvular blood flow,
      wherein the shaft is configured to transduct the captured forces to the apical base plate assembly.

2. The implant of claim 1, wherein each of the plurality of pleats extend radially from first end to second end.

3. The implant of claim 2, wherein adjacent pleats of the plurality of pleats define channels through which blood is allowed to flow.

4. The implant of claim 1, wherein the plurality of pleats are disposed about the entire circumference of the expandable barrier.

5. The implant of claim 1, wherein the expandable barrier, when positioned and in an expanded position in a heart valve, prevents blood flow in a direction going from the second end to the first end of the expandable barrier, and permits blood flow in a direction going from the first end to the second end of the expandable barrier.

6. The implant of claim 1, wherein the expandable barrier further comprises two or more inverted ridges extending beyond the second end of the expandable barrier.

7. The implant of claim 6, wherein each of the two or more inverted ridges curve distally towards the first end.

8. The implant of claim 1, further comprising a plurality of struts extending from the shaft to the expandable barrier.

9. The implant of claim 8, wherein the plurality of struts extending from the shaft to a circumference at the second end of the expandable barrier.

10. The implant of claim 1, wherein the apical base plate assembly comprises a curved shape.

11. The implant of claim 10, wherein the apical base plate assembly is oriented perpendicularly to the shaft.

12. The implant of claim 1, wherein the apical base plate assembly comprises a plurality of cutouts configured to allow ingrowth of tissue.

13. The implant of claim 1, wherein the apical base plate assembly comprises a securement plate and a ball joint.

14. The implant of claim 1, wherein the apical base plate comprises one or more elongated extensions configured to extend over one or more chambers of a heart.

* * * * *